(12) United States Patent
Saigo et al.

(10) Patent No.: US 6,479,702 B1
(45) Date of Patent: Nov. 12, 2002

(54) 3-AMINO-1-INDANOLE, METHOD OF SYNTHESIZING THE SAME AND METHOD OF OPTICAL RESOLUTION

(75) Inventors: Kazuhiko Saigo, Tokyo (JP); Kazushi Kinbara, Tokyo (JP); Yoshiyuki Katsumata, Tokyo (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/110,881

(22) PCT Filed: Sep. 6, 2001

(86) PCT No.: PCT/JP01/07736

§ 371 (c)(1),
(2), (4) Date: Apr. 15, 2002

(87) PCT Pub. No.: WO02/20461

PCT Pub. Date: Mar. 14, 2002

(30) Foreign Application Priority Data

Sep. 6, 2000 (JP) ........................................ 2000-270036

(51) Int. Cl.[7] .............................................. C07B 57/00
(52) U.S. Cl. ...................................... 564/303; 564/308
(58) Field of Search ................................. 564/303, 308

(56) References Cited

U.S. PATENT DOCUMENTS 4,129,561 A    12/1978    Stein et al.

FOREIGN PATENT DOCUMENTS

| JP | 08332095 A | 12/1996 |
| JP | 11511742 T2 | 10/1999 |

*Primary Examiner*—Samuel Barts
(74) *Attorney, Agent, or Firm*—Flynn, Thiel, Boutell & Tanis, P.C.

(57) ABSTRACT

The present invention relates to a compound which is expected to be a synthetic intermediate for medicines and pesticides or a separating agent for chromatography or a enantiomerically resolving agent for racemic bodies. That is, it provides 3-amino-1-indanol represented by the formula (I), a process for synthesizing it, an enantiomerically active compound of 3-amino-1-indanol and a process for enantiomerically resolving 3-amino-1-indanol, and a separating agent for enantiomeric isomers comprising enantiomerically active compound thereof as an effective ingredient.

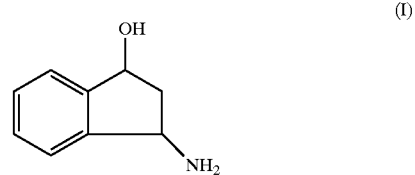

(I)

In the formula, the configuration between OH group and $NH_2$ group are cis-configuration or trans-configuration and the compound may be a racemic body or an enantiomerically active compound.

7 Claims, 1 Drawing Sheet

3-AMINO-1-INDANOLE, METHOD OF SYNTHESIZING THE SAME AND METHOD OF OPTICAL RESOLUTION

This application is a 371 of PCT/JP01/07736 filed Sep. 06, 2001.

TECHNICAL FIELD

The present invention relates to 3-amino-1-indanol which is a novel compound and a process for synthesizing it, further to an enantiomerically active compound of 3-amino-1-indanol and a process for enantiomerically resolving it, and to a separating agent for enantiomeric isomers comprising the enantiomerically active compound as an effective ingredient.

PRIOR ART

Aminoindanols are important intermediates for various fine chemical derivatives including physiologically active substances such as medicines and pesticides. For example, it is disclosed in J. Med. Chem., 35, 2525 (1992), J. Med. Chem., 35, 1702 (1992), J. Med. Chem., 35, 1685 (1992) etc. that cis-1-amino-2-indanol is an effective intermediate for production of anti-HMV drugs.

Moreover, enantiomerically active aminoindanols are effective as separating agents for enantiomerically active carboxylic acids (chiral acids), and JP-A 11-511742 discloses a process for separating chiral acids with 1-aminoindan-2-ol.

3-Amino-1-indanol is a compound also expected to be a synthetic intermediate for medicines and pesticides or a separating agent for chromatography or an enantiomeric resolving agent for racemic bodies, but no body has succeeded in the synthesis thereof and thus it is highly desired to establish the synthetic process.

DISCLOSURE OF THE INVENTION

As a result of the extensive studies for solving the above problems, the present inventors have found out 3-amino-1-indanol which is a novel compound and a convenient process for synthesizing 3-amino-1-indanol using an easily available starting material, further a process for an effective enantiomeric resolution of 3-amino-1-indanol obtained, and a separating agent for enantiomeric isomers comprising an enantiomerically active compound of 3-amino-1-indanol as an effective ingredient. Thus, they have accomplished the present invention.

That is, the present invention provides 3-amino-1-indanol represented by the formula (I):

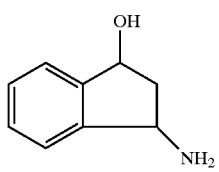

(I)

wherein the configuration between OH group and $NH_2$ group are cis-configuration or trans-configuration and the compound may be a racemic body or an enantiomerically active compound.

Moreover, the present invention provides a process for synthesizing the 3-amino-1-indanol represented by the above formula (I), which comprises the steps of protecting the amino group of β-phenyl-β-alanine represented by the formula (II):

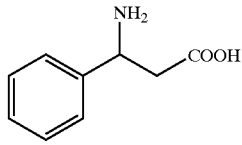

(II)

with a protective group to give a compound represented by the formula (III):

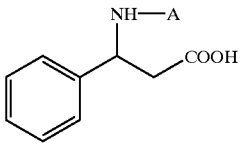

(III)

(wherein A represents RCO- or ROCO- group (wherein R is an alkyl group having 1 to 30 carbon atoms or an aryl group)); subjecting the compound to Friedel-Crafts acylation to give a compound represented by the formula (IV):

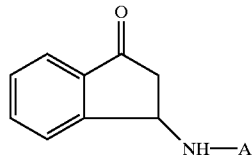

(IV)

(wherein A has the same meaning as above); and then removing the protective group of the compound, followed by reduction. Further, it provides an enantiomerically active compound of 3-amino-1-indanol, and a process for enantiomerically resolving 3-amino-1-indanol, which comprises the steps of treating a mixture of enantiomerically active compounds of 3-amino-1-indanol represented by the above formula (I) with an enantiomerically active carboxylic acid; and then separating formed diastereomer salts from each other, and a separating agent for enantiomeric isomers comprising 3-amino-1-indanol represented by the above formula (I) as the effective ingredient. Furthermore, the present invention provides use of the enantiomerically active compound of the 3-amino-1-indanol represented by the above formula (I) as a separating agent for enantiomeric isomers. In addition, the present invention provides a process for enantiomerically separating a racemic body of the target compound to be separated with 3-amino-1-indanol represented by the above formula (I).

3-Amino-1-indanol of the present invention represented by the formula (I) may be cis-isomer or trans-isomer, or a racemic body or an enantiomerically active compound.

β-Phenyl-β-alanine (II) used as a starting material can be synthesized from benzaldehyde, malonic acid, and ammonium acetate according to a known method. The amino group of the resulting β-Phenyl-β-alanine (II) is protected with a protective group using a compound having a group usable as an amino-protecting group, such as acetic anhydride, benzoyl chloride, 9-fluorenylmethyl chloroformate, benzyloxycarbonyl chloride, or di-t-butyl dicarbonate, to give the compound (III). As the amino-protecting group, preferred is acetyl group or benzoyl group, and more preferred is acetyl group. Then, by subjecting the compound (III) to Friedel-Crafts acylation, an indan skeleton-having compound represented by the formula (IV) can be obtained. Friedel-Crafts acylation is effected by first adding PCl$_5$ to the compound (III), reacting them in a solvent such as ethyl ether or THF, and further reacting the product in a solvent such as methylene chloride at a temperature of 0 to 5° C. with adding AlCl$_3$. A summary of the above reactions is illustrated in the following reaction scheme.

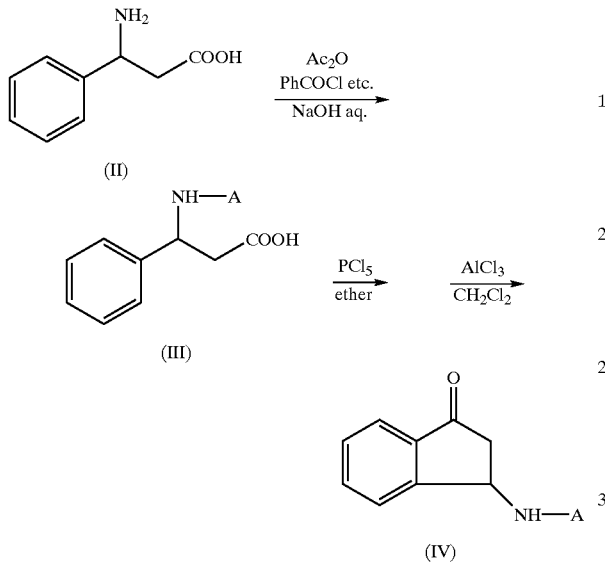

wherein A has the same meaning as above; Ac represents acetyl group and Ph represents phenyl group.

Then, by removing the protective group from the resulting compound (IV) and reduction, 3-amino-1-indanol can be obtained. Depending-on the methods for removal of the protective group from the resulting compound (IV) and reduction, the ratio of the trans-isomer and the cis-isomer can be changed, and thereby the trans-isomer or the cis-isomer can be selectively synthesized. The following will describe the process for synthesizing the trans-isomer and the cis-isomer in detail.

First, the following illustrates a summary of the process for synthesizing (±)-trans-3-amino-1-indanol (racemic body) (I-1) from the compound (IV).

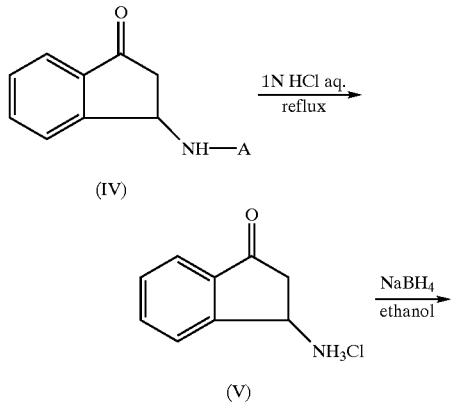

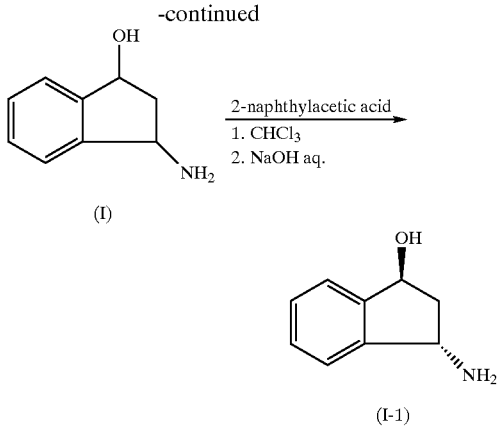

wherein A has the same meaning as above.

Namely, the trans-isomer of 3-amino-1-indanol represented by the formula (I) can be predominantly obtained in a ratio of trans:cis=3:1 by heating the compound (IV) obtained in the above under reflux under an acidic condition, to give a hydrochloride salt (V) through removal of the protective group, and further reducing the carbonyl group. The reduction of the carbonyl group to hydroxyl group is conducted by means of a metal hydride reagent such as sodium borohydride.

By purifying the mixture (I) of the trans- and cis-isomers, (±)-trans-3-amino-1-indanol (racemic body) (I-1) can be obtained. As the purifying method, used is preferably made of a method of forming a salt of the mixture (I) with a 2-arylcarboxylic acid such as 2-naphthylacetic acid, heating the salt under reflux, and then allowing to stand at room temperature. By this method, only the salt of the trans-isomer can be selectively crystallized. Subsequently, the above trans-isomer (I-1) can be obtained by treating the salt with an aqueous solution of an alkali selected from sodium hydrogencarbonate, potassium hydrogencarbonate, sodium carbonate, potassium carbonate, sodium hydroxide potassium hydroxide etc, and then extracting with a suitable organic solvent.

Next, the following illustrates a summary of the process for synthesizing (±)-cis-3-amino-1-indanol (racemic body) (I-2) from the compound (IV).

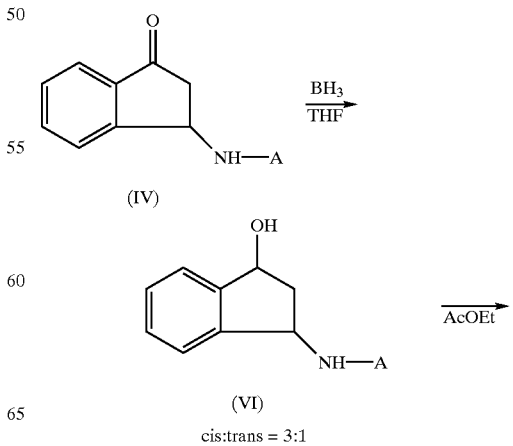

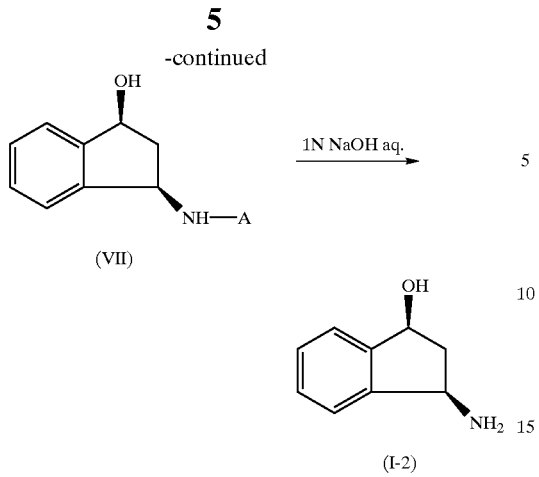

wherein A has the same meaning as above; Ac represents acetyl group; and Et represents ethyl group.

Namely, by dissolving the compound (IV) in a suitable solvent and subjecting it to reduction with, for example, sodium borohydride, cis-isomer of (±)-N-acyl-3-aminoindan-1-ol (VI) can be predominantly obtained in a ratio of cis:trans=3:1. At that time, the reaction solvent is preferably tetrahydrofuran (THF). Moreover, the reaction temperature is preferably from −100 to −50° C. Then, the resulting mixture (VI) of the cis- and trans-isomers are purified by a chromatography, recrystallization or the like, to give (±)-cis-N-acyl-3-aminoindan-1-ol (VII).

(±)-cis-3-Amino-1-indanol (racemic body) (I-2) can be obtained by heating the resulting (±)-cis-N-acyl-3-aminoindan-1-ol (VII) in a suitable basic organic solvent under reflux and then extracting with a suitable solvent. At that time, the basic organic solvent is preferably a sodium hydroxide-ethanol mixed solvent and the extracting solvent is preferably methylene chloride.

The enantiomeric resolution of the racemic body of 3-amino-1-indanol can be conducted according to a diastereomer salt method using an enantiomerically active carboxylic acid. The usable enantiomerically active carboxylic acid is not particularly limited but it is preferable to use dibenzoyltartaric acid because an enantiomerically active compound can be efficiently obtained.

The solvent used at the enantiomeric resolution is not particularly limited but preferred is a water-ethanol mixed solvent. The crystallizing temperature may be in the range of 0 to 60° C., preferably the range of 10 to 40° C. If necessary, the crystallized diastereomer salt may be recrystallized to give a crystalline diastereomer salt having a higher enantiomeric purity.

The enantiomerically active compound of 3-amino-1-indanol obtained as above is useful as a separating agent for enantiomeric isomers, particularly an enantiomeric resolving agent for the racemic body of an enantiomerically active carboxylic acid.

In the enantiomeric resolution of an enantiomerically active carboxylic acid using 3-amino-1-indanol, an enantiomerically active carboxylic acid can be obtained by the method of mixing an enantiomerically active compound of 3-amino-1-indanol and the racemic body of an enantiomerically active carboxylic acid in a suitable solvent and then precipitating a diastereomer salt. In particular, a carboxylic acid having an aryl group at the 2-position can be preferably enantiomerically resolved.

Novel 3-amino-1-indanol of the present invention is an extremely important compound as an synthetic intermediate for medicines and pesticides, especially for medicines.

Furthermore, enantiomerically active 3-amino-1-indanol can be widely utilized also as a separating agent for enantiomerically active carboxylic acids.

EXAMPLES

Figure 1:
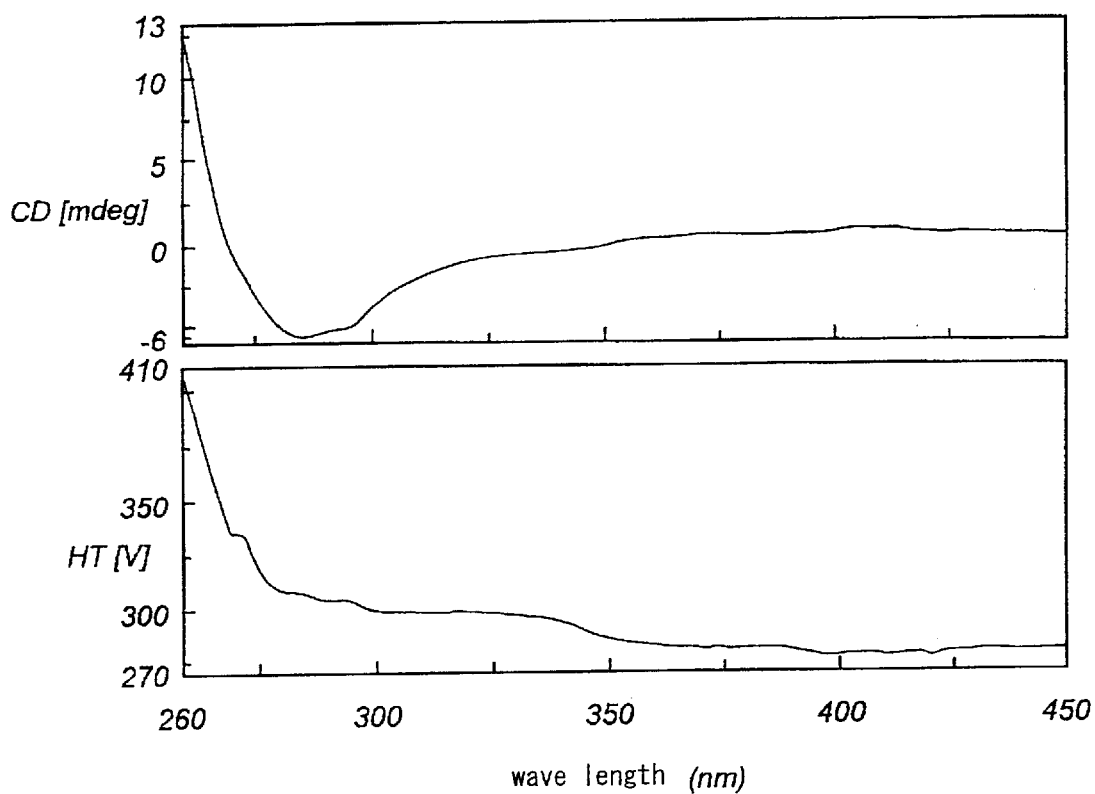
FIG. 1 is a CD spectrum of an enantiomerically active precedent component-(I-2) obtained in (3) of Example 2.

The following will describe the present invention in detail with reference to Examples. The present invention is not restricted by these Examples.

Example 1

Synthesis of trans-3-amino-1-indanol (1) Synthesis of (±)-β-phenyl-β-alanine (II)

To 270 mL of ethanol were added 115 g (1.08 mol) of benzaldehyde, 113 g (1.08 mol) of malonic acid, and 167 g (2.16 mol) of ammonium acetate, followed by stirring for 5 hours under heating and refluxing. Precipitated white crystals were filtered and the filtrate was recrystallized from a water-ethanol mixed solvent (1:4, 2.5 L), to give 85.14 g of the title compound (II) as white crystals (yield 48%).

(2) Synthesis of (±)-(N-acetyl)-β-phenyl-β-alanine (III)

Fifty grams (0.33 mol) of the compound (II) obtained in (1) was dissolved into 200 mL of water into which 13.32 g (0.32 mol) of NaOH had been dissolved. To the mixture was added 78 g (0.77 mol) of acetic anhydride, followed by stirring at room temperature for 4 hours. Precipitated white crystals were filtered and washed well with water, and then dried in vacuo under heating, to give 55.85 g of the title compound (III) (yield 89%).

(3) Synthesis of (±)-(N-acetyl)-3-aminoindan-1-one (IV)

After drying in vacuo under heating, in an eggplant-shape flask whose atmosphere had been replaced with argon were placed 55.00 g (0.27 mol) of the compound (III) obtained in (2) and 55.31 g (0.27 mol) of $PCl_5$. Thereto were added 160 mL of ethyl ether and 40 mL of THF, followed by stirring at 0° C. for 30 minutes and then at room temperature for 5 hours. Subsequently, the solvent was evaporated and the residue was washed with ethyl ether (3×100 mL). Ethyl ether was again evaporated and then the residue was dried in vacuo. Thereto was added 300 mL of methylene chloride and then 177 g (1.35 mol) of $AlCl_3$ was slowly added thereto at 0° C. under stirring. After stirring at room temperature for further 2.5 hours, the reaction mixture was poured into a 2 L Erlenmeyer flask containing 1 L of ice. After the confirmation of completion of the reaction of $AlCl_3$, the mixture was extracted with methylene chloride (4×400 mL). The organic layer was dried over sodium sulfide, the drying agent was removed by filtration, then, the solvent was evaporated, and the residue was dried in vacuo, to give 48.70 g of the title crude product (IV). The product was separated and purified by silica gel column chromatography (ethyl acetate) and further recrystallized from ethyl acetate (300 mL), to give 38.24 g of the title compound (IV) (yield 76%).

Melting point: 155–158° C.

$^1$H-NMR ($CDCl_3$): δ=2.055 (s, 3H), 2.468 (dd, 1H, J=3.3, 19.2), 3.216 (dd, 1H, J=7.8, 19.2), 5.681 (dt, 1H, J=3.3, 7.8), 5.956 (s, 1H), 7.453–7.757 (m, 4H).

(4) Synthesis of (±)-3-aminoindan-1-one hydrochloride (V)

To 300 mL of 1N hydrochloric acid aqueous solution was added 18.26 g (0.097 mol) of the compound (IV) obtained in (3), followed by stirring for 5 hours under heating and refluxing. After the confirmation of completion of the reaction, the solvent was evaporated and the residue was dried in vacuo, to give 17.51 g of the title compound (V).

Melting point: 257° C.

$^1$H-NMR (D$_2$O): δ=2.826–2.900 (m, 1H), 3.353 (dd, 1H) 5.158–5.184 (m, 1H), 7.686–7.941 (m, 4H)

IR (KBr): 3450, 3000, 2900, 1730, 1600, 1490, 1370, 1290, 1260, 780 cm$^{-1}$.

(5) Synthesis of (±)-trans-3-amino-1-indanol (I-1)

Into 450 mL of ethanol was dissolved 17.51 g of the compound (V) obtained in (4). After cooling to 0° C., 2.76 g (0.072 mol) of NaBH$_4$ was added gradually thereto, followed by stirring overnight. Most of the solvent was evaporated, 100 mL of water was added thereto, and then extracted with methylene chloride (5×200 mL). The organic layer was dried over sodium sulfate. After filtering off the drying agent, the solvent was evaporated and the residue was dried in vacuo, to give 7.38 g of (±)-3-amino-1-indanol (I). Further, the aqueous layer was evaporated and the residue was dried in vacuo, followed by adding 200 mL of ethanol to the residue. After cooling to 0° C., 1.22 g (0.072 mol) of NaBH$_4$ was added thereto, followed by stirring overnight. Subsequently, most of the solvent was evaporated, 100 mL of water was added to the residue, and then the mixture was dried over sodium chloride. After filtering off the drying agent, the solvent was evaporated and the residue was dried in vacuo, to give 5.97 g of (±)-3-amino-1-indanol (I), whereby 13.35 g (0.089 mol) of (±)-3-amino-1-indanol (I) (a mixture of trans-isomer:cis isomer=3:1). Thereto was added 17.5 g (0.094 mol) of 2-naphthylacetic acid and then 1 L of chloroform, and the whole was stirred under heating and refluxing for several minutes and then allowed to stand at room temperature. Precipitated white salt was filtered and dried in vacuo. Thereto was added 100 mL of 1N NaOH aqueous solution to make the liquid basic and, after extracted with methylene chloride (5×300 mL), the organic layer was dried over sodium sulfate. After filtering off the drying agent, the product was dried in vacuo and further recrystallized from benzene-petroleum ether (5:1, 300 mL), to give 7.02 g of the title compound (±)-(I-1) as white crystals (two-step yield 49%).

Melting point: 108–110° C.

$^1$H-NMR (D$_2$O): δ=1.583 (br s, 3H), 2.056 (dt, 1H, J=6.3, 13.7), 2.461 (ddd, 1H, J=3.0, 6.3, 13.7), 4.641 (t, 1H, J=6.3), 5.336 (dd, 1H, J=3.0, 6.3), 7.306–7.426 (m, 4H)

IR (KBr): 3350, 3300, 3125 (br), 2925, 2700, 1650, 1320, 1300, 1040, 990, 780 cm$^{-1}$.

(6) Enantiomeric resolution of (±)-trans-3-amino-1-indanol (I-1)

Into a water-ethanol mixed solvent (1:1, 630 mL) were dissolved 7.52 g (0.05 mol) of the compound (±)-(I-1) obtained in (5) and 19.25 g (0.051 mol) of L-(+)-dibenzoyltartaric acid under heating, followed by allowing to stand at room temperature. Precipitated crystals were filtered, further recrystallized three times from a water-ethanol mixed solvent (1:1, 150 mL), filtered, and dried in vacuo, to give enantiomeric pure (1S, 3S)-trans-3-amino-1-indanol-L-(+)-dibenzoyltartaric acid salt (5.30 g). Thereto was added 50 mL of 1N NaOH aqueous solution to make the liquid basic, and extracted with methylene chloride (4×200 mL). The organic layer was dried over sodium sulfate, the drying agent was removed by filtration, the solvent was evaporated, and the residue was dried in vacuo. The product was recrystallized from benzene-hexane (1:1, 40 mL), to give 1.10 g of (1R,3R)-trans-3-amino-1-indanol (I-1) as colorless crystals (yield 29%, enantiomeric purity 99% e.e. or more).

Melting point: 112–113.5° C.

[α]=39.3 (c=1.00, ethanol)

On the other hand, after evaporating the filtrate from the first recrystallization, the liquid was basified with 50 mL of 1N NaOH aqueous solution and extracted with methylene chloride (4×200 mL). The organic layer was dried over sodium sulfate, the drying agent was removed by filtration, then the solvent was evaporated, and the residue was dried in vacuo. Thereto was added 7.20 g (0.019 mol) of D-(−)-dibenzoyltartaric acid, and the product was recrystallized three times from a water-ethanol mixed solvent, to give enantiomeric pure (1R, 3R)-trans-3-amino-1-indanol-D-(−)-dibenzoyltartaric acid salt (3.15 g). Thereto was added 50 mL of 1N NaOH aqueous solution to make the liquid basic, and the mixture was extracted with methylene chloride (4×200 mL). The organic layer was dried over sodium sulfate, the drying agent was removed by filtration, the solvent was evaporated, and the residue was dried in vacuo. The product was recrystallized from benzene-hexane (1:1, 40 mL), to give 1.43 g of (1S,3S) -trans-3-amino-1-indanol (I-1) as colorless crystals (yield 38%, enantiomeric purity 99% e.e. or more).

Melting point: 113.5–114° C.

[α]=38.1 (c=1.00, ethanol)

The enantiomeric purity was determined on HPLC under the following conditions.

Column: CROWNPAK CR (manufactured by Daicel Chemical Industries, Ltd.)

Flow rate: 0.5 mL/minute

Detecting wavelength: 200 nm

Developing solvent: pH 2 HClO$_4$ aqueous solution

Peaks: precedent one (1S, 3S)-(I-1), subsequent one (1R, 3R)-(I-1)

Example 2

Synthesis of cis-3-amino-1-indanol (1) Synthesis of (±)-cis-N-acetyl-3-amino-1-indanol (VII)

In 100 mL of THF was dissolved 8.0 g (0.042 mol) of the compound (IV) obtained in (3) of Example 1. After cooling to −78° C., 42 mL (0.042 mol) of 1.01M BH$_3$/THF was gradually added thereto, followed by stirring overnight. The reaction was terminated by adding 1N hydrochloric acid aqueous solution, and then extracted with methylene chloride. The organic layer was dried over sodium sulfate, the drying agent was removed by filtration, the solvent was evaporated, and the residue was dried in vacuo, to give 6.54 g of (±)-N-acetyl-3-amino-1-indanol (a mixture of cis isomer:trans-isomer=3:1). The product was further purified by silica gel column chromatography (eluent: ethyl acetate), to give 3.33 g of white crystals. Subsequently, the crystals were twice recrystallized from ethyl acetate (90 mL), to give 1.45 g of the title compound (±)-(VII) (two-step yield 18%).

Melting point: 170–172° C.

$^1$H-NMR (CDCl$_3$): δ=1.80 (dt, 1H, J=5.7, 8.1), 2.01 (s, 3H), 2.57 (d, 1H, J=6.3), 2.92 (ddd, 1H, J=6.6, 7.5, 13.8), 5.15 (dd, 1H, J=6.3, 13.1), 5.30 (dd, 1H, J=7.5, 13.5), 7.32–7.46 (m, 4H)

IR (KBr): 3400, 3300, 1640, 1550, 1280, 1060, 990, 780, 760 cm$^{-1}$.

(2) Synthesis of (±)-cis 3-amino-1-indanol (I-2)

Into a 1N sodium hydroxide-ethanol mixed solvent (100 mL:10 mL) was dissolved under heating 4.09 g (0.021 mol) of (±)-(VII) obtained in (1), followed by heating under reflux for 6 days. After cooling to room temperature, the mixture was extracted with methylene chloride (4×200 mL). The organic layer was dried over sodium sulfide, the drying agent was removed by filtration, the solvent was evaporated, and then the residue was dried in vacuo, to give 2.41 g of the title compound (±)-(I-2) (yield 75%).

Melting point: 67–75° C.

$^1$H-NMR (CDCl$_3$): δ=1.64 (dt, 1H, J=6.6, 1.2), 2.13 (br s, 3H), 2.81 (dt, 1H, J=6.6, 13.2), 4.24 (t, 1H, J=6.3), 5.05 (t, 1H, J =6.0), 7.302–7.443 (m, 4H)

IR (KBr): 3350, 1580, 1460, 1340, 1050, 770, 740 cm$^{-1}$ (3) Enantiomeric resolution of (±)-cis-3-amino-1-indanol (I-2)

The compound (±)-(I-2) obtained in (2) was enantiomerically resolved under the following HPLC conditions.

Column: CROWNPAK CR(+) (manufactured by Daicel Chemical Industries, Ltd.)

Flow rate: 1.0 mL/minute

Detecting wavelength: 220 nm

Developing solvent: pH 1.9 HClO$_4$ aqueous solution

Temperature: 10° C.

Each fraction of the precedent component-(I-2) and subsequent component-(I-2) fractionated on HPLC was, after concentration, basified by the addition of 10% sodium hydroxide aqueous solution and then extracted with chloroform, to give aimed enantiomerically active precedent component-(I-2) (yield 28%, enantiomeric purity 97.3% e.e.) and enantiomerically active subsequent component-(I-2) (yield 18%, enantiomeric purity 95% e.e.). The enantiomeric purity was determined under the same conditions as in Example 1.

The results of IR, $^1$H-NMR, and CD measurements of the enantiomerically active precedent component-(I-2) are shown in the following. Also, CD spectrum of the enantiomerically active precedent component-(I-2) is shown in FIG. 1.

IR (neat): 3350, 1645, 1580, 1455, 1325, 1090, 1045, 760, 735 cm$^{-1}$.

$^1$H-NMR (300 MHz) (CDCl$_3$): δ=1.63 (ddd, 1H, J=6.6, 6.6, 6.6 Hz), 2.43 (bs, 3H +H$_2$O), 2.73 (ddd, 1H, J =6.6, 6.6, 6.6 Hz), 4.21 (dd, 1H, J=6.6, 6.6 Hz), 5.02 (dd, 1H, J=6.6, 6.6 Hz), 7.2–7.5 (m, 4H) ppm CD (CHCl$_3$, 5.4×10$^{-4}$ M, band width: 1.0 nm, response: 1 second, sensitivity: Low, measuring range: 450–260 nm, data uptake interval: 0.5 nm, scanning rate: 100 nm/minute, integrating number of times: 8 times): –5.6 mdeg (285 nm), –5.0 mdeg (296 nm)

Application Example

Using (1S, 3S)-trans-3-amino-1-indanol obtained in (6) of Example 1 and, for comparison, (1S, 2S)-trans-1-amino-2-indanol and (1S, 2S)-trans-2-amino-1-indanol shown in Table 1 as separating agents, enantiomeric resolution of racemic bodies of target compounds 1 and 2 to be separated shown in Table 1 was conducted according to a diastereomer crystallization method.

Namely, in the case of the separating agent of the present invention, equimolar amounts of the separating agent and the racemic body of the target compound to be separated were dissolved into acetonitrile and the solution was cooled to 4° C. to precipitate crystals. Moreover, in the case of the separating agent for comparison, equimolar amounts of the separating agent and the racemic body of the target compound were dissolved under heating in a water-ethanol mixed solvent (1:1) and the solution was allowed to stand at 26° C. to precipitate crystals. The results are shown in Table 1.

Table 1

| Optical separating agent | Target compound to be separated | |
|---|---|---|
| | 1 | 2 |
| 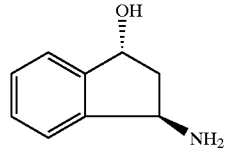<br>Product of the present Invention | 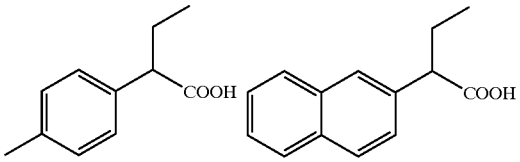<br>yield (%) 95<br>e.e. (%) 22 (S)<br>efficiency 0.21 | yield (%) 93<br>e.e. (%) 39<br>efficiency 0.36 |
| 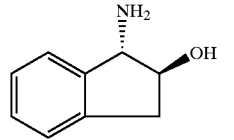<br>Comparative Product | not crystallized | yield (%) 42<br>e.e. (%) 61<br>efficiency 0.26 |

-continued

| Optical separating agent | Target compound to be separated | | | |
|---|---|---|---|---|
| | 1 | | 2 | |
| 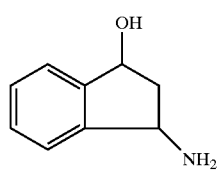<br>Comparative Product | yield (%)<br>e.e. (%)<br>efficiency | 99<br>3 (R)<br>0.03 | yield (%)<br>e.e. (%)<br>efficiency | 51<br>4<br>0.02 |

From the results shown in Table 1, the separating agent of the present invention can efficiently separate the racemic bodies of the target compounds to be separated as compared with the comparative separating agents.

What is claimed is:

1. 3-Amino-1-indanol represented by the formula (i):

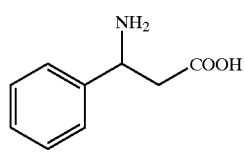

(I)

wherein, the configuration between OH group and $NH_2$ group are cis-configuration or trans-configuration; and the compound may be a racemic body or an enantiomerically active compound.

2. A process for synthesizing the 3-amino-1-indanol as claimed in claim 1, which comprises the steps of protecting the amino group of β-phenyl-β-alanine represented by the formula (II):

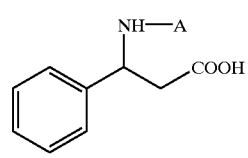

(II)

with a protective group to give a compound represented by the formula (III):

(III)

(wherein A represents RCO- or ROCO- group (wherein R is an alkyl group having 1 to 30 carbon atoms or an aryl group)); subjecting the compound to Friedel-Crafts acylation to give a compound represented by the formula (IV):

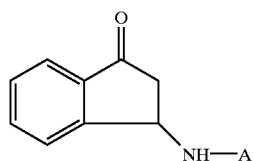

(IV)

(wherein A has the same meaning as above); and then removing the protective group of the compound, followed by reduction.

3. The 3-amino-1-indanol as claimed in claim 1, which is an enantiomerically active compound.

4. A process for enantiomerically resolving 3-amino-1-indanol, which comprises the steps of treating a mixture of enantiomerically active compounds of the 3-amino-1-indanol as claimed in claim 1 with an enantiomerically active carboxylic acid; and then separating the resulting diastereomer salts from each other.

5. A separating agent for enantiomeric isomers comprising the enantiomerically active compound of 3-amino-1-indanol as claimed in claim 1 as an active ingredient.

6. Use of the enantiomerically active compound of 3-amino-1-indanol as claimed in claim 3 as a separating agent for enantiomeric isomers.

7. A process for enantiomerically separating a racemic body of the target compound to be separated with the enantiomerically active compound of 3-amino-1-indanol as claimed in claim 3.

* * * * *